United States Patent [19]

Ausman et al.

[11] 4,039,682
[45] Aug. 2, 1977

[54] METHOD AND COMPOSITION FOR RELIEF OF BACK PAIN

[75] Inventors: Robert K. Ausman, Long Grove; Ivan J. Stern, Morton Grove, both of Ill.

[73] Assignee: Baxter Travenol Laboratories, Inc., Deerfield, Ill.

[21] Appl. No.: 671,470

[22] Filed: Mar. 29, 1976

[51] Int. Cl.$^2$ ............................................ A61K 31/195
[52] U.S. Cl. ................................................... 424/319
[58] Field of Search .......................................... 424/319

[56] References Cited
PUBLICATIONS

Hashimoto et al., Biochemistry, vol. 7, No. 7, pp. 2469–2475 (1968).

Kapsalis et al., Journal of Laboratory and Clinical Medicine, vol. 83, pp. 532–540 (1974).

Primary Examiner—Stanley J. Friedman
Attorney, Agent, or Firm—Garrettson Ellis; Paul C. Flattery

[57] ABSTRACT

Back pain and other symptoms of intervertebral disk disease are relieved by injecting into the diseased intervertebral disk of the back an aqueous solution of, for example, in each milliliter of solution: 3.5 mg. of cysteine hydrochloride monohydrate; 0.37 mg. of disodium edetate dihydrate; 1 mg. of sodium bisulfite, 20 mg. of sodium iothalamate; and sufficient sodium hydroxide to provide a pH of about 6.5 to the solution. The solution is free of proteolytic enzymes.

16 Claims, No Drawings

METHOD AND COMPOSITION FOR RELIEF OF BACK PAIN

BACKGROUND OF THE INVENTION

For several years, a formulation containing a proteolytic enzyme (chymopapin) has been utilized in extensive clinical trails in a surgical procedure, involving the injection of such a formulation into an intervertebral disk of the back, to relieve chronic back pain and other symptoms of disk disease, such as partial paralysis of the legs.

Recent references on the subject include the article by Kapasalis, et al. from the *Journal of Laboratory and Clinical Medicine* Vol. 83, pages 532–540 (1974); and pages 374–383 in the *Journal of Neurosurgery* Vol. 42, No. 4 (1975).

While the procedure has been very successful in its extensive clincial trail, it has an admitted disadvantage: approximately 1 percent of the patients which received the intervertebral injection with chymopapain solution suffer anaphylatic shock as a side effect. Furthermore, because of the danger of anaphylactic shock, it is at the present deemed inadvisable for a patient to receive more than one chymopapain intervertebral injection in his lifetime. Accordingly, the present expert judgment is that further problems with an intervetebral disk of the back in the same patient will have to be handled surgically. This is generally a very severe and sometimes dangerous procedure, which is accompanied by a separate group of potentially sever risks to the patient.

During the course of such a clinical trial, a double-blind study was administered by us, comparing a chymopapain-based back injection solution with a control injection solution, free of proteolytic enzymes.

Most suprisingly, the data indicated to us that the control solution, free of proteolytic enzymes, performed effectively in the cure of back pain, as did the chymopapain solution. These results were completely unexpected, and the physicians and scientists involved with the clinical trial were initially at a loss for an explanation.

This discovery is a signification advance in the art of injection for intervertebral disk treatment, because a solution which is free of proteolytic enzymes, and is still effective, can achieve the desirable results of the prior art injection material with an extreme reduction in the risk of anaphylactic shock. Also, there appears to be no theorectical basis for limiting the use of the formulation of this invention to a single use in the lifetime of the patient. Accordingly, repeated treatment as necessary can be utilized by means of this invention.

DESCRIPTION OF THE INVENTION

In accordance with this invention, back pain may be relieved by injecting into an intervertebral disk of the back formulation which comprises an effective dosage of an aqueous solution of cysteine, the formulation being free of proteolytic enzymes.

More specifically, the formulation may, for example, contain from 3 to 10 mg. of cysteine per ml. of solution, and typically 3 to 5 mg., preferably in the form of cysteine hydrochloride. The solution may also contain other materials as desired, for example buffers, X-ray contrast media, various activators as desired, various materials for adjusting the ion balance of the solution, antibiotics or other medicaments, and the like. For example, from 15 to 25 mg. of an X-ray contrast medium such as sodium Iothalamate (sodium 5-acetamido-N-methyl-2,4,6-triiodoisophthalamate) may be present per ml. of solution. Similarly, from 0.3 to 0.4 mg. of disodium edetate may be added per ml. of solution, as well as from 0.8 to 1.2 mg. of sodium bisulfite per ml. of solution.

It is preferable for the cysteine, or an equivalent non-toxic organic sulfhydryl reducing agent, to be present in combination with sodium Iothalamate. For example, from 3 to 50 mg. of cysteine and at least 10 mg. of sodium Iothalamate may be present per ml. of solution.

Sufficient alkali such as sodium hydroxide may be added to provide a generally neutral pH. A generally neutral pH is a pH which does not excessively irritate the tissues into which the solution is injected, and is preferably about 6 to 7, typically not on the alkaline side. As stated before, the formulation is free of proteolytic enzymes.

Without wishing to be limited by any theory of operation of the method and formulations of this invention, it is believed that the cystein ingredient, being a non-toxic, organic sulfhydryl compound, acts as a protein splitting agent in the nucleus pulposus of the intervertebral disk by reducing sulfur-sulfur linkages, resulting in the relief of back pain and other symptoms in a majority of patients. The cysteine may be administered in the form of derivative compounds and salts such as cysteine hydrochloride, N-acetylcysteine, or sodium cysteine.

Also, it is believed that any nontoxic, organic sulfhydryl reducing agent, preferably having a molecular weight of no more than about 400 can be utilized as a substitute for cysteine in the formulation of this invention, for example: organic thio acids such as thioglycollic acid, thiolactic acid, or 4-thiobutyric acid; salts or thio acids such as sodium thioglycollate or potassium thiolactate; sulfhydryl-containing peptides such as glutathione; thioalcohols and thiopolyols such as thioethanol or thioglycerol; carbohydrate derivatives such as thioglucose; and other materials such as Cleland's reagent (diethiothreitol).

The following specific embodiment illustrating the use of the formulation of this invention is offered for illustrative purposes only, and is not intended to limit the scope of this invention, which is as defined in the claims below.

EXAMPLE 1

In preparation for a double-blind clinical study of the effects of a chymopapain solution (solution A) upon injection into intervertebral disks, compared with the formulation of this invention (solution B), sterile water for injection was purged with nitrogen gas for fifteen minutes, and overlaid with nitrogen in a covered container. The purged water was then cooled to approximately 5° C.

Bulk lots of solution A and solution B were prepared as follows: to 3 liters of the purged, chilled water for injection, 14 grams of cysteine hydrochloride monohydrate and 1.48 grams of disodium edetate dihydrate were added, and dissolved with minimal stirring. To both solutions A and B, the pH was adjusted to approximately 6.5 by adding 1 N sodium hydroxide. Stirring was performed with a stream of nitrogen gas. Thereafter, to each solution, 4 grams of sodium bisulfite were added, the material also being dissolved with minimal stirring.

Then, to a solution A there was added $4.6 \times 10^7$ chymopapain units (about 92 grams of material). The solution was stirred gently to dissolve the material as above.

To solution B, there was added 100 ml. of 80 percent sodium Iothalamate injection U.S.P. solution, containing 80 grams of sodium Iothalamate, instead of the chymopapain.

For both solutions, the pH was predetermined and readjusted with sodium hydroxide if necessary to about 6.5. Cold, sterile water for injection, at 5° C., and purged as described above, was then added to each of solutions A and B to give a final volume of 4 liters to each lot of solution.

Each lot of solutions A and B was sterilized by filtration through a 0.22 micron membrane filter under nitrogen pressure or a low vacuum. The filtrate was collected in a reservoir through a closed, sterile system.

Samples of solutions A and B were then metered into sterile, glass vials and sealed under sterile conditions, the vials being closed with latex diaphragms for later access by an injection needle. The vials were closed with a metal outer closure under sterile conditions.

The vials of solutions A and B were then used in a double-blind, randomized study utilizing a number of major university medical facilities and a government military medical facility. The patients ranged from ages 21 to 65, having radicular pain, with previous extensive non-surgical treatment having been unsuccessful, and with positive myelogram and physical signs of intervertebral disk disease, compatible with the X-ray findings.

Twenty-four patients were tested by intervertebral injection with the chymopapain Solution A, while 30 patients were tested with the Solution B of this invention.

Nine patient code breaks, defined herein as treatment failures, occurred with patients treated with chymopapain solution, while eight occurred with respect to the solution of this invention.

In the subjective judgments of the physicians involved, of the patients treated with solution A containing chymopapain, approximately 60 percent of the treatments were successful as of 8 weeks following their respective treatments. With respect to the patients treated with solution B, in accordance with this invention, approximately 68 percent of the treatments were judged as successful by the respective physicians as of 8 weeks following the treatment.

A telephone poll of the patients themselves was also performed. Between 80 and 90 days after treatment, they were asked to judge their pain on a scale of 1 (no pain) to 9 (extremely severe pain) both before the treatment and after the treatment.

Of those patients which have been treated with solution A, the average rating of their pain prior to treatment was 6.25. The average rating of their pain after the treatment was 3.90.

Of those patients being treated with solution B, in accordance with this invention, the average rating of their pain before the operation was 5.95. The average rating of their pain after the operation was 2.78.

EXAMPLE 2

One hundred five patients in roughly equal groups were treated respectively with an intervertebral disk injection with either solution A or solution B as prepared in Example 1 above. After 180 days had passed following treatment, 59 percent of those patients who had received treatment with solution A reported that their symptoms were significantly improved compared with their condition prior to treatment. Fifty percent of the patients having received solution B reported significant improvement.

The data of this Example includes the case histories of the patients of Example 1.

Accordingly, the composition of this invention appears to be at least about equal in effectiveness to a clinical chymopapain solution formulated for the same purpose. It is superior to the chymopapain solution in that the risk of anaphylactic shock is essentially eliminated, thus reducing the risk of treatment for all patients, and also permitting the treatment of patients with known or suspected allergic sensitivity to proteolytic enzymes.

That which is claimed is:

1. The method of relieving back pain and related symptoms which comprises injecting into an intervertebral disk of the back a formulation which comprises an effective dosage in aqueous solution of cysteine, said formulation being free of proteolytic enzymes and having a generally neutral pH.

2. The method of claim 1 in which said cysteine is present in the form of 3 to 50 mg. of cysteine hydrochloride per ml. of said solution.

3. The method of claim 1 in which from 15 to 25 mg. of sodium Iothalamate are present per ml. of said solution.

4. The method of claim 1 in which from 0.3 to 0.5 mg. of disodium edetate is present per ml. of said solution.

5. The method of claim 1 in which from 0.5 to 1.5 mg. of sodium bisulfite is present per ml. of said solution.

6. The method of claim 1 in which the pH of said solution is from 6 to 7.

7. The method of claim 3 in which from 0.3 to 0.5 mg. of disodium edetate are present per ml. of said solution.

8. A formulation for injection into an intervertebral disc of the back for relief of back pain and related symptoms, which comprises: an aqueous solution of an effective dosage of cysteine, said formulation being free of proteolytic enzymes and having a generally neutral pH, and containing from 0.3 to 0.5 mg. of disodium edetate per ml. of said solution.

9. The formulation of claim 8 in which said cysteine is present in the form of 3 to 50 mg. of cysteine hydrochloride per ml. of said solution.

10. The formulation of claim 8 in which the pH of said solution is from 6 to 7.

11. The formulation of claim 8 in which 0.05 to 1.5 mg. of sodium bisulfite is present per ml. of said solution.

12. The formulation of claim 8 in which from 15 to 25 mg. of sodium Iothalamate are present per ml. of said solution.

13. A formulation for injection into an intervertebral disk of the back for relief of back pain and related symptoms, which comprises: an aqueous solution comprising from 3 to 5 mg. per ml. of solution of cysteine hydrochloride; from 0.3 to 0.4 mg. per ml. of solution of disodium edetate; from 0.8 to 1.2 mg. per ml. of solution of sodium bisulfite; and from 15 to 25 mg. per ml. of solution of sodium Iothalamate, said solution having sufficient sodium hydroxide added thereto to provide it with a pH of 6 to 7, said formulation being free of proteolytic enzymes.

14. A formulation for injection into an intervertebral disc of the back, for relief of back pain and related symptoms, which comprises: an aqueous solution of an effective dosage of cysteine, in combination with sodium Iothalamate present in a concentration of at least 10 mg. per ml. of solution, said formulation being free of proteolytic enzymes and having a generally neutral pH.

15. The formulation of claim 14 in which from 3 to 50 mg. of cysteine hydrochloride are present per ml. of said solution.

16. The formulation of claim 15 in which from 15 to 25 mg. of sodium Iothalamate are present per ml. of said solution.